United States Patent [19]
Stocker

[11] Patent Number: 5,794,847
[45] Date of Patent: Aug. 18, 1998

[54] AIR ASSISTED INSECT DISPENSING APPARATUS AND DELIVERY PROCESS

[76] Inventor: Russell Stocker, 3412 Laguna Ave., Davis, Calif. 95616

[21] Appl. No.: 738,415

[22] Filed: Oct. 25, 1996

[51] Int. Cl.$^6$ .................................................. A62C 5/02
[52] U.S. Cl. ........................... 239/8; 239/171; 239/172; 239/654
[58] Field of Search ..................... 239/8, 77, 152–154, 239/171, 172, 650, 651, 653, 654, 659, 663, 668, 683

[56] References Cited

U.S. PATENT DOCUMENTS

| | | | |
|---|---|---|---|
| 978,615 | 12/1910 | Miller | 239/668 |
| 3,872,012 | 3/1975 | Endicott | 210/297 |
| 3,968,933 | 7/1976 | Waldrum | 239/171 |
| 3,994,437 | 11/1976 | Kitterman | 239/171 X |
| 4,089,441 | 5/1978 | Cole et al. | 239/654 X |
| 4,260,108 | 4/1981 | Maedgen, Jr. | 239/171 |
| 4,475,819 | 10/1984 | Balmer | 239/654 X |
| 4,487,365 | 12/1984 | Sperber | 239/8 |
| 4,966,329 | 10/1990 | Show | 239/650 |
| 5,148,989 | 9/1992 | Skinner | 239/171 |
| 5,190,225 | 3/1993 | Williams | 239/154 X |
| 5,213,271 | 5/1993 | Uribe et al. | 239/654 |
| 5,288,028 | 2/1994 | Spivak et al. | 239/683 |

*Primary Examiner*—Andres Kashnikow
*Assistant Examiner*—Steven J. Ganey
*Attorney, Agent, or Firm*—Mark C. Jacobs, Esq.

[57] ABSTRACT

An apparatus for the metered delivery of beneficial insects such as but not limited to Trichogramma adaptable for mounting on a tractor, airplane, or a backpack blower carried by ground personnel. The apparatus employs a binder injection system for impact upon the metered beneficial insects in a moving airstream for delivery to specific targets. The process of delivery constitutes the controlled metering of a desired amount of a beneficial insect into an airstream for impact by a measured amount of a binder solution such that the insects become coated, after which the insects are then delivered to their target area by a high velocity airstream.

30 Claims, 5 Drawing Sheets

AIR ASSISTED INSECT DISPENSING APPARATUS AND DELIVERY PROCESS

FIELD OF THE INVENTION

The present invention relates generally to the field of insect dispensing, and, more specifically, to the process of metered dispensing of insects from airplanes or blowers onto walnut trees and other substrates. The invention also relates to compositions of binder coated insects and the method of making them.

BACKGROUND OF THE INVENTION

It is well known that insects can injure people and destroy their food supplies. In early days, controlled fires were started to drive insects such as locusts away with smoke and more recently a variety of insecticides such as DDT have been developed. Unfortunately DDT and many of the early poisons for insects were not selective. The existence of mass fish kills due to pesticide residues is well documented. Therefore since the outlawing of DDT in the U.S.A., the E.P.A. and other nongovernment groups have been looking for and finding replacement techniques for pesticides and pesticide management programs.

The Codling moth, *Cydia pomonella*, is a major exotic pest of walnuts, apples and pears in California and elsewhere in the United States. It has become a major problem in three quarters of the California counties where walnuts are grown. Codling moths produce three generations per year and larval damage from the first generation is believed to be responsible for nut drop in June. Nut meat damage caused by third generation larvae is seen at the harvest and is more easily quantified. Since California produces virtually all of the commercially produced walnuts in the United States with over 205,000 acres in 20 counties dedicated to walnut production there is indeed significant interest in controlling this pest.

One way that has been developed is to use a natural predator of the pest to destroy the pest., i.e., the coddling moth, which can reek havoc upon a walnut orchard if left unchecked, and which is one of the many lepidopterous pests encountered in northern California. The predator of choice by applicant is the Trichogramma, a small parasitic wasp. This tiny wasp was believed to be a natural enemy of the codling moth since it was known that Trichogramma will attack the eggs of other lepidoptera.

The use of Trichogramma to fight the codling moth in walnut orchards has been previously reported. The currently accepted technique for distribution is to ship refrigerated pupae of the TG inside parasitized grain moth eggs, to the customer. The refrigeration slows down the maturation. Large sheets of cardstock or paper are coated with a glue as by brushing or sponging and globs of the parasitized eggs placed thereon. The large sheets of substrate are cut up by hand and little squares are stapled to individual leaves of the walnut tree, wrapped around twigs, and stapled in place, placed or attached to drinking cups and wedged into or attached to locations on trees. There are several problems associated with this technique. First, mature walnut trees are 12 to 18 meters tall, so the placement of the beneficial insect paper squares relatively near the ground, i.e., 2 meters up, does not concentrate the predator where the codling moth deposits its eggs, in the upper reaches of the tree. The prior art hand placement method, is labor super intensive and the technique does not allow rapid coverage during short weather related optimum application periods. Further, the cardstock squares present concentrated masses of eggs, poorly protected from ants, earwigs and other predators, due to their location, thereby reducing the percent of pupae that can mature to do their job. Since the shape of a tree is random, uniform horizontal dispersion of the squares is totally impossible. Thus areas will be overly populated, and area will be under populated with the beneficial insect. Thus excess placement is required at more cost to overcome these deficiencies, at still higher cost.

Applicant was of the belief that an improved method of delivery was possible, using spray techniques. Thus applicant set out to provide new insect compositions as well as a replacement mode of delivering Trichogramma hereinafter Tg, singular or Tgs plural, to fight the codling moth in walnut trees. Since walnut trees were to be the target to be treated, he also went about determining whether other pests of the walnut tree could be counteracted by the same new method of delivery of a predator to the target area.

Aerial spraying methods were well known to applicant, and indeed there are numerous patents dealing with the aerial spraying of beneficial insects. Thus a patent search revealed the following U.S. Patents:

U.S. Pat. No. 4,260,109 Maedgen
U.S. Pat. No. 5,148,989 Skinner

Other patents that turned up during the course of the search included:

U.S. Pat. No. 3,484,062 Johnson
U.S. Pat. No. 4,537,333 Bjerregaard
U.S. Pat. No. 1,749,504 C. L. Pelton
U.S. Pat. No. 2,730,402 A. A. Whiting, Jr. et al
U.S. Pat. No. 2,772,061 J. M. Sellers
U.S. Pat. No. 2,986,360 L. D. Rutten
U.S. Pat. No. 3,476,337 W. D. Cornett, Jr.
U.S. Pat. No. 3,525,473 P. R. Pickell
U.S. Pat. No. 3,777,978 Manicatide et al
U.S. Pat. No. 3,847,113 Andreev et al None of these references either alone, or in combination anticipate or render obvious the apparatus, method of delivery, or the composition to be disclosed herein.

It is a first objective to provide a metering dispenser for beneficial insects for delivery by a high speed airstream.

It is an object of the invention to provide a novel apparatus for the delivery of parasitized grain moth eggs of the wheat moth for delivery by airplanes.

It is another object to provide a novel apparatus which can be modified for delivery of Trichogramma and other beneficial insects by a man/woman carried blower or from a crop dusting airplane.

It is a further object to provide a metering system for the delivery of parasitized eggs.

It is a still further object to provide an improved apparatus for the delivery of Trichogramma pupae to walnut trees.

It is a yet further object to provide a new process for the delivery of parasitized eggs and other beneficial insects.

It is indeed an additional object to provide a process for the delivery of Trichogramma pupae to walnut trees to fight the coddling moth.

Other objects of the invention will in part be obvious and will in part appear hereinafter.

The invention accordingly comprises (1) the apparatus possessing the construction, combination of elements and arrangement of parts; (2) the method involving the several steps and the relation and order of one or more of such steps with respect to each of the other steps for delivery of the beneficial pest compositions according to the invention; (3) the several steps and the relation and order of one or more of such steps with respect to the others for the manufacture of the compositions of this invention; and (4) the compositions possessing certain features and properties; all of which are exemplified in the following detailed disclosure, and the scope of the application of which will be indicated in the appended claims.

For a fuller understanding of the nature and objects of the invention reference should be made to the following detailed description, taken in conjunction with the accompanying drawings.

SUMMARY OF THE INVENTION

Figure 1:
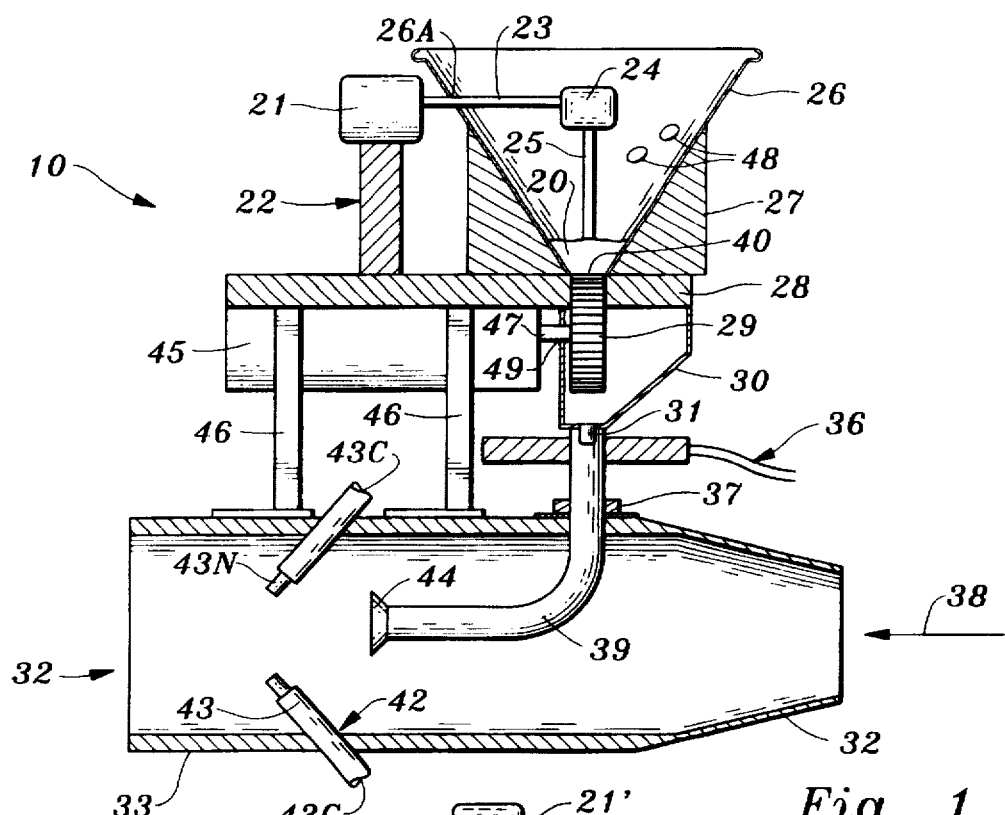
FIG. 1 is a diagrammatic sectional view of the basic apparatus of this invention.

The apparatus of this invention is a metering dispenser for beneficial insects such as but not limited to Trichogramma, which apparatus employs a binder injection system for impact upon the metered beneficial insects in a moving airstream for delivery to specific targets. The delivery can be from an airplane or from ground personnel.

The process of delivery constitutes the controlled metering of a desired amount of a beneficial insect into an airstream for impact by a measured amount of a binder solution such that the insects become coated, after which the insects are then delivered to their target area by a high velocity airstream.

All of these activities can be carried out by introducing the beneficial insects into a hopper, metering the addition thereof into an airstream using a spur gear or other limiting device such as a rotor, introducing mucilage or some other non-lethal binder onto the moving insects and ejecting the binder coated insects into an airstream for delivery to a target, be it a specific plant, or to a piece of paper.

DESCRIPTION OF THE PREFERRED EMBODIMENT

Beneficial Insect Preparation

The desired Trichogramma wasp is a natural enemy of various lepidoptera (moths and butterflies). In order to propogate the Trichogramma wasp are propagated as follows. Eggs of the grain moth are collected from nature by individuals and companies called insectories. While the grain moth is a pest to wheat, rye, etcetera, it is not a pest to the walnut tree. From these eggs, large numbers of the grain moth are raised under controlled conditons and the eggs are again collected. The eggs are put into areas known as stinging chambers. Female Trichogrammas are introduced and permitted over a one to three day period to sting or oviposit the eggs of the wheat moth with their own eggs. The eggs of the Trichogramma hatch first and the larvae of the Trichogramma feed on the nutrients found in the egg of the grain moth.

The Trichogramma larvae then goes into the pupae stage, ready to emerge as adults. It is these pupae within the eggs of the host grain moth that are to be delivered according to this invention to the walnut trees, such that when the Trichogrammas emerge, as fully developed parasitic wasps, they can then attack the eggs of the pest lepidoptera, which in this case is the codling moth which is highly detrimental to the walnut crop. While there may be some nectar or dew available from certain plants or aphids, to serve as food for the Trichogrammas usually such is not the case. Either way the life cycle of the adult Trichogramma is between 1 and about 3 days, so it is important to introduce the pupae of the Trichogramma into the "infected area" at the right time.

It is to be understood, that even if every egg of the host lepidoptera; namely, the grain moth is not oviposited, whereby a small amount of the grain moths actually become born, this phenomenon is not considered to be a problem as the grain moth is NOT a pest of the walnut tree.

It is seen therefore that the product to be delivered here is A within B. That is, the pupae of the Trichogramma within the egg of the host, the grain moth.

This combination however, is NOT the inventive composition used in the process of this invention. My new composition, which can arise during the carrying out of the process of this invention, can also be prepared by other methods to be discussed. My new composition is also disclosed and claimed in my copending patent application, (Attorney Docket No. 1525B) U.S. Ser. No. 08/738,414 filed concurrently hereiwth.

It is also to be noted that while most of my research has been caried out using Trichogramma parasitized eggs, my compositon invention is not limited thereto. Thus, I have found as will be discussed, that lace wings and other beneficial insects in their egg stage can be similarly treated with a binder solution according to my method for delivery to a specific plant or other target such as sheets of paper.

The discussion now turns to FIG. 1. In this figure the basic apparatus of this invention is shown in a somewhat sectional view. Apparatus 10 is a multi-component article that includes a metering device for the introduction of solids, here beneficial insects, into an airstream, where the insects are coated with a binder solution for delivery by high speed air to a target. Apparatus 10 comprises a hopper 26, which may be funnel shaped as depicted or it may be any other shaped bowl having a depressed central bottom exit 40 for easy unloading, and which is open at the top for the loading of material such as parasitized eggs 48, therein.

Hopper 26 is retained in position by hopper mount 27 which may be made of any suitable material such as plastic or metal, as can be the hopper itself A motor 21 is mounted on a suitable support 22, which in turn is attached by means not seen to chassis 28. Motor 21 includes a shaft 23 connected thereto and high shaft passes through aperture 26A of the hopper. The shaft 23 is connected at its oposite end in a conventional manner to a gear box 24 which is suspended within the confines of the hopper 26. Also connected to the gear box 24 is the shaft 25 of a stirrer 20. This stirrer is a wire member preferably having one upward depending and one downward depending paddle-like member thereon to agitate the hopper contents to prevent clogging. Other configurations for the stirrer are also contemplated.

Mounted directly beneath the constricted opening 40 of the hopper 26, is a metering device, 29, for periodically dispensing a determinable finite amount of the contents of the hopper into the collection bin, 30 for a gravity feed through the spout 31 into the J-tube, also called the delivery tube, 39 and down into the chamber. The metering device here is a spur gear 29 attached to a shaft 49 connected to the motor 45. Note that the side wall of the collection bin 30 is preferably angled, to force any contents to fall toward the spout 31.

The purpose of the collection bin is to provide an intermediate means to collect a small amount of the insect for gravity feed through the spout 31. By providing a narrower opening through the spout, than the opening at the bottom of the hopper, close control of the feed of the insects to the chamber to be discussed below can be achieved. Also this narrower opening enhances the ability of the optical sensor to function. From a practical point of view there is never any real build up of insect volume within the collection bin, no matter how fast or slow the metering transpires.

Figure 8:
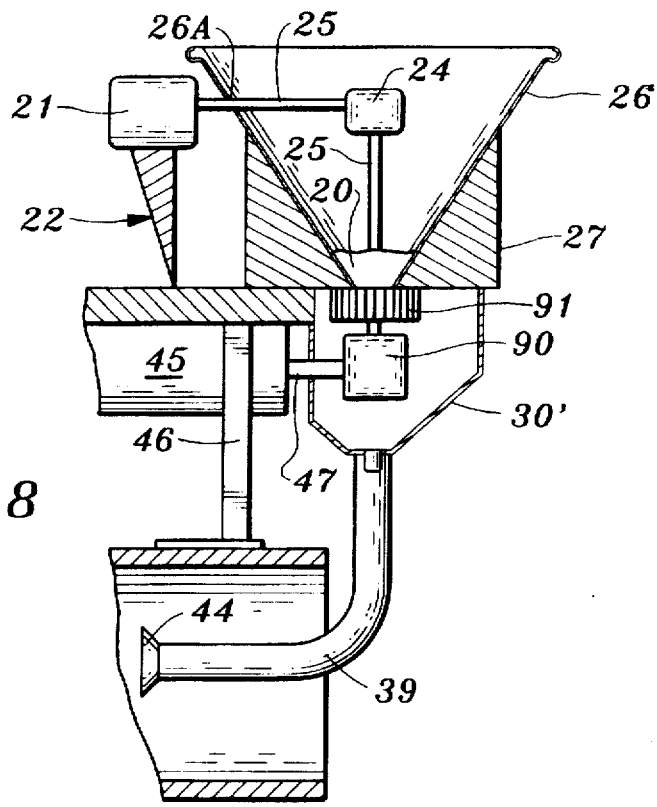
FIG. 8 is an elevational view of a variant spur gear metering device.

Other metering devices can also be used. For example the spur gear oriented horizontally as shown in FIG. 8, would serve in like fashion to open and close the opening 40 of the hopper 26. The rotating disk of FIG. 9 serves the same purpose, as would a rotor.

Deviating momentarily, it is seen in FIG. 8 that the motor 45 is similarly supported by legs 46 as in FIG. 1, and also has a shaft 47. The shaft 47 is connected to a gear box 90 to which in turn is connected the horizontally oriented spur gear 91. As the gear moves past the opening 40, the opening is alternatively opened-close-opened-closed. Note that the collection bin has been reshaped and enlarged to accommodate the gear box 90. Accordingly the bin has been renumbered as 30'. Note also the absence of the optional optical sensor.

Figure 9:
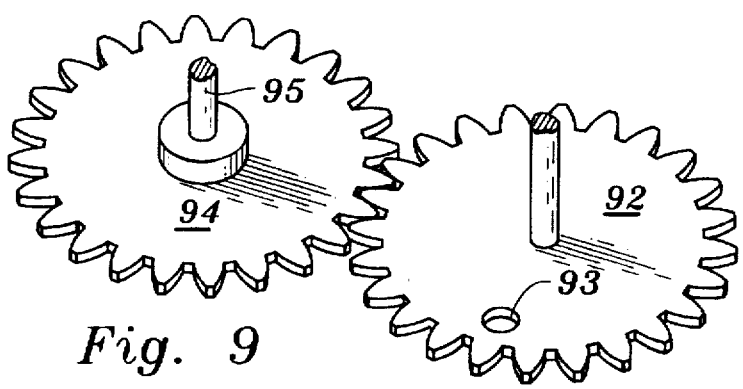
FIG. 9 is a top plan view of a rotating disk metering device.

In FIG. 9, an apertured disk 92 having at least one aperture 93 engages a driving disk, 94, either frictionally, or by the engagement of gear teeth on each, to rotate the aperture past the opening 40. The shaft 95 of the driving disk would be connected to a motor unseen. The mounting of such a metering system is within the skill of the art.

Figure 7:
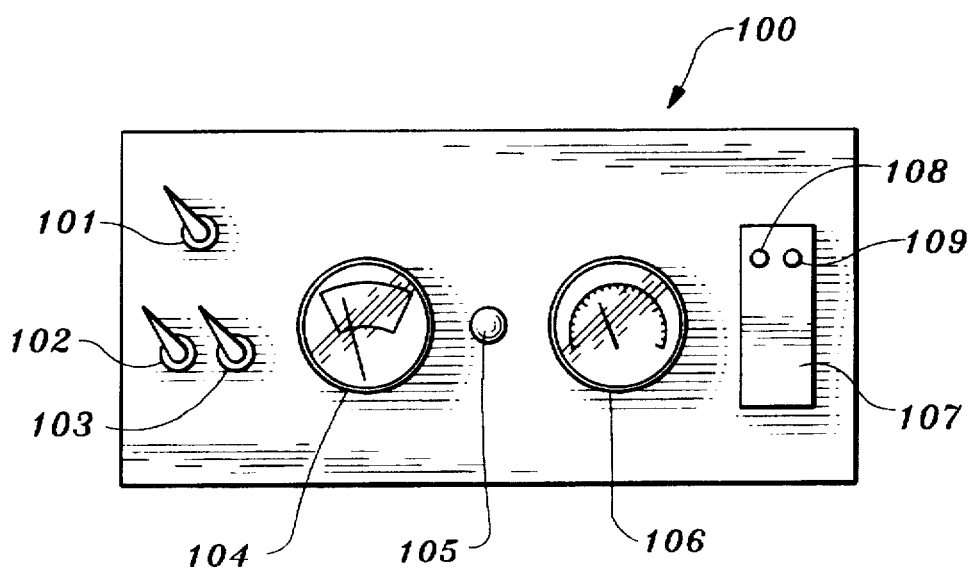
FIG. 7 is a pictorial rendition of the controls utilized by a pilot to operate the apparatus of this invention when it is mounted under the wing or elsewhere on an airplane.

The discussion returns now to FIG. 1. Seen here circumscribing the spout 31, and abutting the hopper is J-tube 39 which preferably has a flared front edge, 44 to ensure dispersion. The J-tube may be entirely clear, but if the optional sensor 36 is employed, then the area passing through the annular optical sensor should be clear in order for the sensor to recognize movement of material from the spout into the J-tube 39. The sensor is a powered electonic indicator to verify flow no- flow of material from the spout. Optical sensors of this nature are well known in the art and are readily available in the marketplace from several manufacturers. The sensor is activated if employed from the panel of the cockpit of the plane. Reference is made to FIG. 7 to be discussed infra.

The J-tube 39 is glued or otherwise attached to the J-tube retainer 37 which is mounted to the body of the delivery chamber 32. This chamber has a main portion 33 and a reverse venturi front portion 34 to slow down the incoming airstream 38. Chamber 32 may be round tubular or square tubular as may be desired. Note also that the motor supports 46 which are attached to the motor 45 are also attached as by screws, glue or otherwise to the main portion of the chamber 33. Chamber 33 may be made of plastic such as ABS (acrylonitrile-butadiene-styrene) or metal such as aluminum or steel as may be desired.

While shown as an integral unit, the front portion 34 may be a separate piece threadedly or otherwise engaged to the main portion 33. This junction would take place between the two imaginary dashed lines 333 and 334. Since such is so readily understood, no separate illustration of that fact is deemed necessary.

Figure 3:
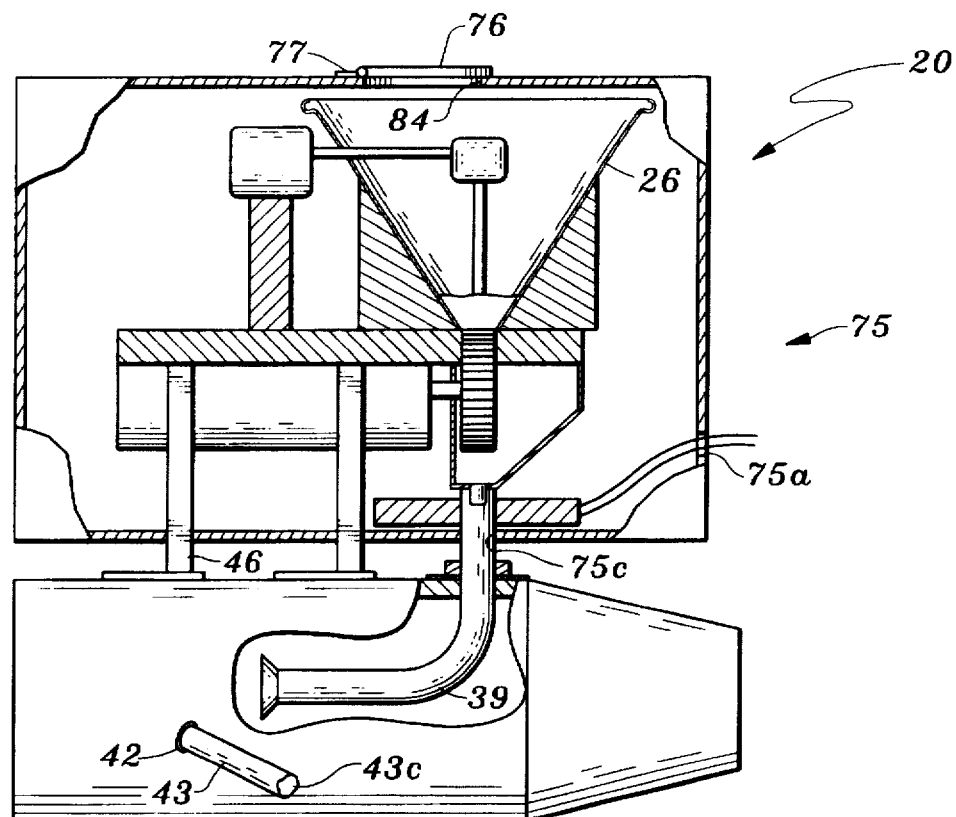
FIG. 3 is a diagrammatic view of the apparatus adapted for use by aerial spray personnel.

Disposed through suitable openings 42 in the wall of the main portion 33 of the chamber are a pair of opposed injectors 43. Each of these includes a nozzle 43N thereon. As seen in FIG. 1, these nozzles enter from the top and bottom of the chamber, but there is no criticality to such entry. Side entry as illustrated in FIG. 3 is also contemplated. Note too that the injectors 42 are shown to terminate on the end opposite the injector, in a coupling 43C. At least one injector is required to transmit the binder solution as discrete droplets.

Figure 2:
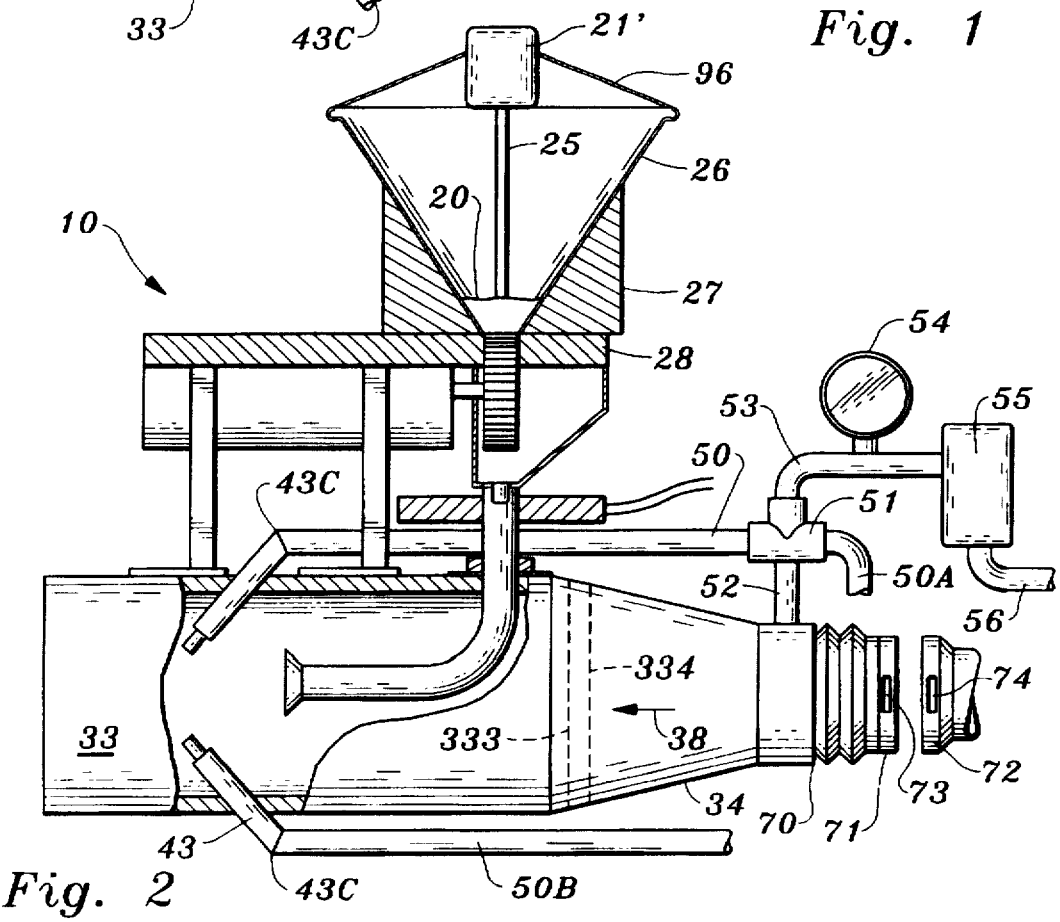
FIG. 2 is a view similar to FIG. 1, wherein the apparatus has been adapted for use by ground personnel with personal air sources.

Reference is now made to FIG. 2, wherein like parts bear like numbers, and as such need not be again discussed. Prior to discussing the proximal end of the injector at the coupling 43C, it is to be noted that there is a slight structural change or variant in the disposition of the motor to operate the stirrer. Here the shaft 25 is connected directly to a top mounted motor 21" with the elimination of the gear box 24. A wire retainer means 96 encircles the motor and is secured to the hopper to prevent vibration of motor 21 and to provide stability thereto.

In FIG. 2, each coupling is seen to be connected to a hose 50, which in turn is connected to a Tee 51. Since for ease of illustration one such hose is discontinuous, the segment attached to the coupler is designated 50B, while the segment attached to the Tee is designated 50A. In reality 50A and 50 are attached to each other.

The Tee 51 is seen to have two outlets, each connected to one hose 50. The inlet side of the Tee is fluidly connected to line 53 which has an optional pressure gauge 54 connected in line thereto. This conventional adjustable pressure gauge is used to set and to check the spray pressure of the fluid being introduced through the injectors. The proximal end of line 53 is connected to a regulator-pump 55 fluidly connected via fluid line 56 to a source such as any conventional vessel or tank of fluid binder, not seen.

The unit seen in this figure is adapted for attachment to a personal hand carried blower. The attachment to convert from a basic unit for mounting on a plane or a tractor consists of the the extension 70 which attaches as by a a threaded connection or friction fit as may be desired to the inlet end of the venturi. Tee mount 52 may be bolted, clamped or otherwise attached to the extension. A bellows coupling 71 is secured to the extension, and said coupling 71 includes a bayonet connector adapted to engage the bayonet connector 74 of of the blower coupling 72.

While bayonet connections are shown, and which are well known to those in the interchangeable lens for camera art, other types of connections of a releaseable nature may be employed to join a blower, such as made by Paramount, Toro and other garden hardware product manufacturers. Such blowers are readily available in the marketplace.

Figure 6:
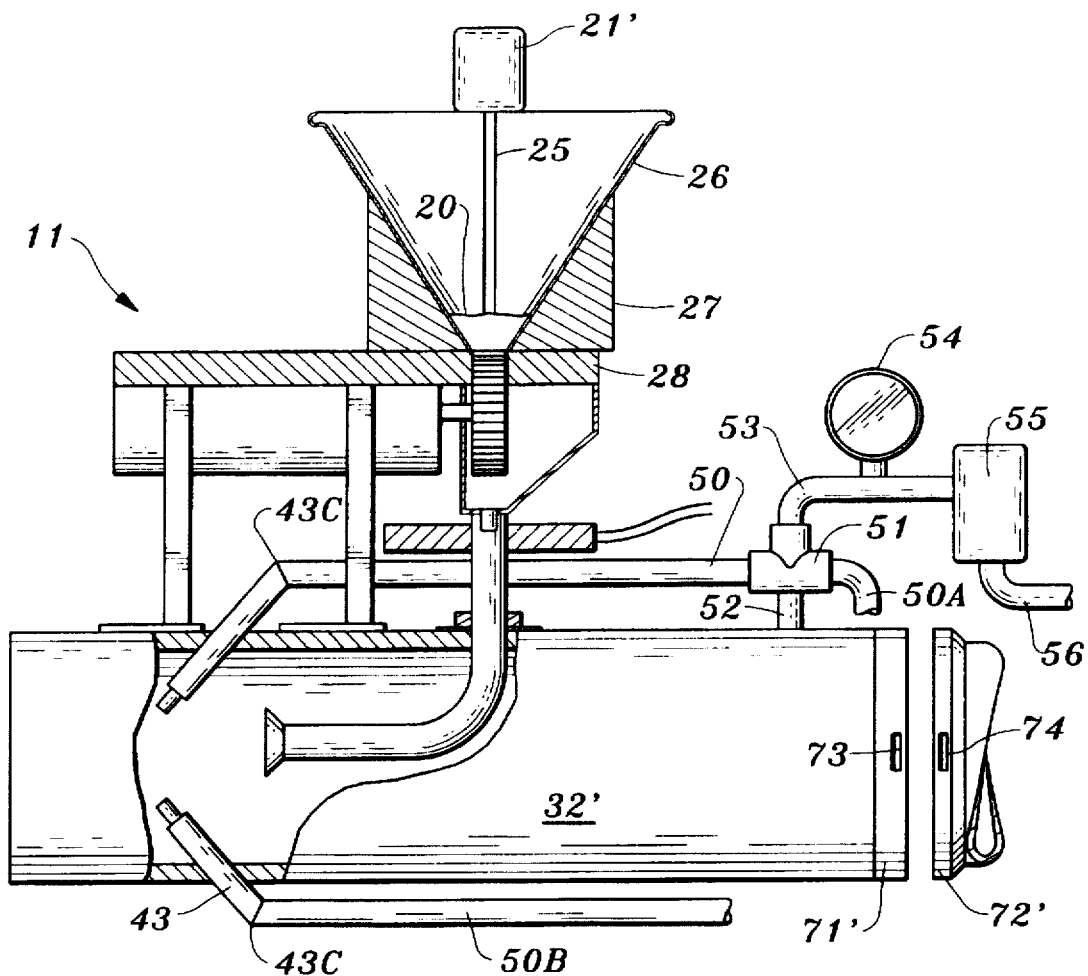
FIG. 6 is a variant of the apparatus of FIG. 2, also for use by ground personnel.

In FIG. 6 an apparatus according to the invention, but modified for a commercial blower unit is seen. Again like numbers refer to like parts, and like parts will not be repeatedly discussed.

In this figure, the chamber is designated 32' as it is entirely of one cross-section. Thus the embodiment of the invention is designated 11. No reverse venturi to slow down the incoming air is emplyed, because the exit speed of air emanating from commercial blowers can be regulated to a desired speed such as to injure the eggs being discharged into the airstream through the J-tube. Thus coupling 71' is attached in a conventional fashion to the inlet end of the chamber. This coupling has a similar bayonet 73 for mating engagement of the bayonet mount 74 of coupler 72. As is seen coupling 72 and coupling 72' of the respective blowers, each have a slightly larger cross section to fit over the coupling attached to the chamber. Refer again to FIG. 2.

Whether the metered dispensing apparatus is to be mounted on a plane, tractor or hand blower, the direction of the airstream is always the same. The air moves from the inlet, past the J-tube and then past the injectors. But note that when mounted on a plane or tractor, the inlet 34 faces forward, as air rushes in and throught the inlet 34, is slowed down and then moves out the main portion 33. But when mounted on a hand blower, the inlet faces the operator, as the source of air is from behind, i.e., in the blower unit carried by the operator. But the airstream movement stays the same.

The discussion moves to FIG. 3. Here the apparatus 20 is seen. The injector 43 is seen to be disposed within a side opening 42S, such that the second and opposed injector is not visible in this view. This slightly different location is required due to the employement of a housing for the balance of the apparatus. This housing 75 is seen to be a box, having side walls, a bottom wall with suitable cutouts 75C for the motor supports 46 and the J-tube 39, as well as an aperture 75A for the electrical leads of the optical sensor 36 in the front wall. The top wall thereof has an opening 84 therein for access to the hopper 26. This opening is covered over by a hinged optionally lockable hatch 76, which is pivotally mounted by hinges 77. The housing 75 provides enhanced cosmetic appeal, as well as preventing possible tampering with any of the componets or the contents of the hopper. The apparatus when housed can be mounted on a tractor, on an airplane or to a hand blower. The leads of the sensor are connected to a power source.

Figure 4:
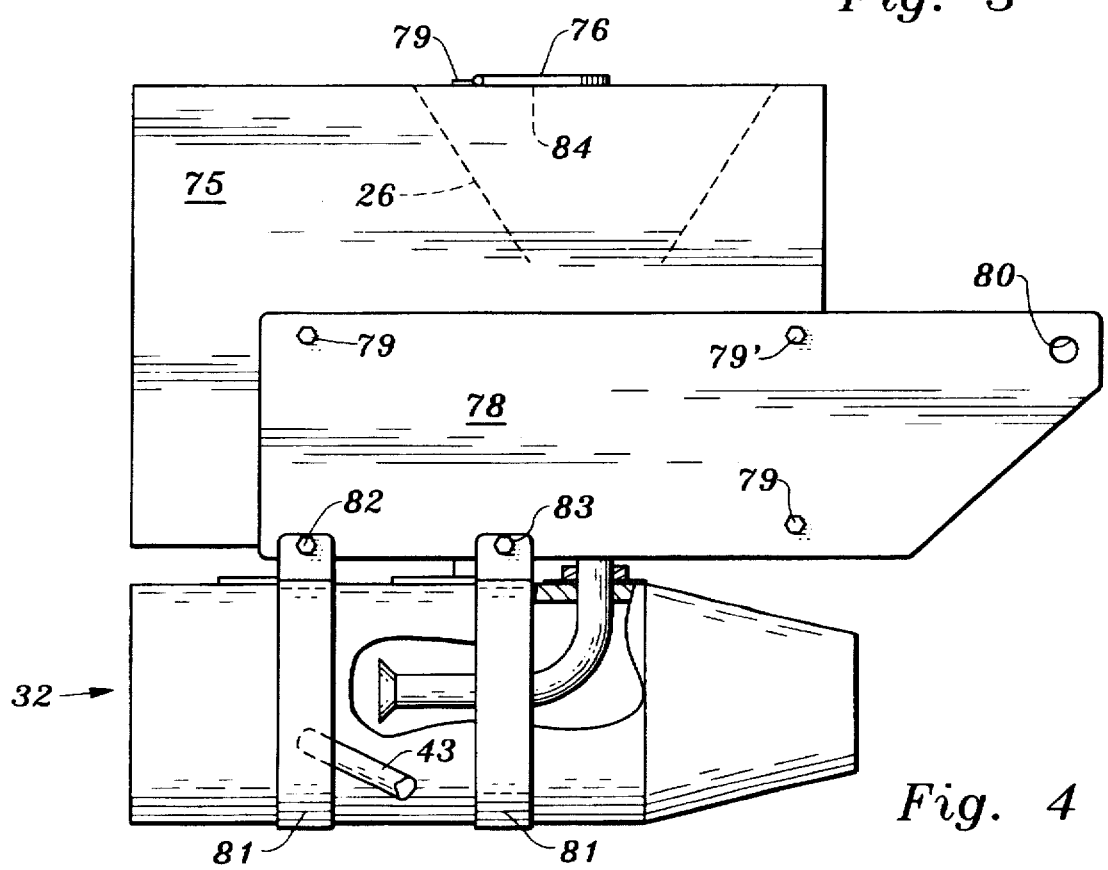
FIG. 4 is a side elevational view of a mount system for attaching the apparatus of this invention to an airplane.

In FIG. 4 there is depicted a mount plate 78 which is shown bolted to the housing by self-tapping bolts 79, one of which is disposed in each bore 79'. At least one bolt hole 80 is provided for the bolting of the mount plate 78 to a suitable part of the airplane or tractor by which the apparatus is to be carried. In order to provide additional security to the chamber 32, one or more, here two straps 81 are disposed around the chamber 32 and attached by a bolt and nut 82 to the mount plate 78 through aperture 83 of the strap which communicates with an aligned throughbore in the mount plate, not seen.

Figure 10:
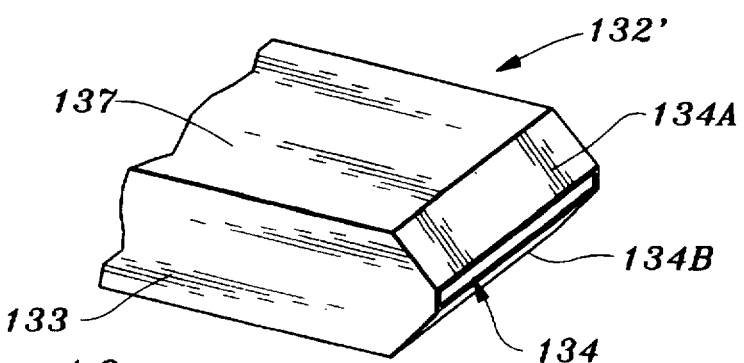
FIG. 10 is a perspective view of an alternate chamber suitable for air delivery of the coated compositions of this invention.

In FIG. 10, there is shown an alternate configuration for the mixing chamber. None of the other components such as the hopper or its input into the chamber are shown. This alternate generally rectangular version is designated 132' with the main portion being 133 and the integrated inlet being 134. Note that the forward diverging panels 134A and B still create the reverse venturi effect to slow down the speed of the incoming air.

Figure 5:
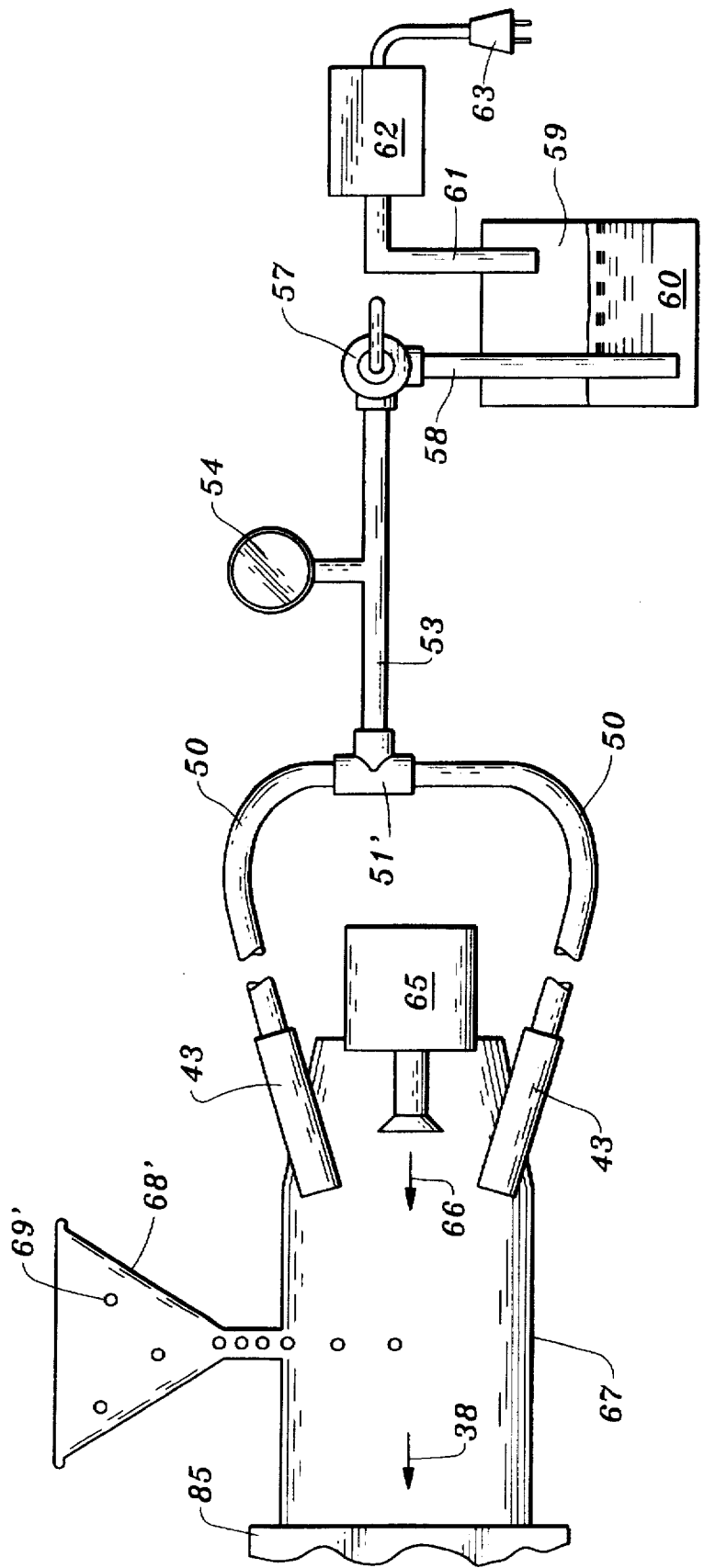
FIG. 5 is diagrammatic view illustrating the process of this invention and illustrating more clearly certain components forming a part of the apparatus of this invention.

The discussion now moves to FIG. 5. This figure is a diagrammatic depiction of the process making the new compositions of this invention. An electrical air pump 62 which has a corded plug 63 is fluidly connected to vessel 59 via fluid line 61 for the input of air. A solution of binder agent 60, of a nature to be described infra is pumped out line 58 by the air which displaces the binder solution in the closed vessel. A combination inline regulator and on-off valve 57 ensures a steady flow of liquid. The binder 60 moves past a pressure gauge through line 53 to Tee 51'. This Tee is a 3 way ball valve that can split the solution such that part of it is fed to each line 50 or to only one of the lines 50 for fluid delivery to the respective injector 43 in communication with that specific line 50. Thus the equivalent of single line operation can be achieved by using this type of ball valve tee.

An air blower 65 delivers air 66 (represented by the double arrow) into a mix chamber 67, in the same direction as the fluid is being injected from injectors 42. From an input hopper 68, beneficial insects 69 are introduced into the chamber by gravity or other means known to the art. These beneficial insects are impacted by the spray 60 from the injectors 43 and the air 66 from the blower 65 moves the coated insects in the direction of the air flow 38 toward a collection target 85. This target can be a cardboard stratum or it can be a tree, or a plant, or the interior surface of a box, or even simple butcher paper as may be desired where the binder coated beneficial insects that constitute the product of this invention are collected.

The reader's attention is drawn to the comparison of FIG. 5 to FIG. 1. While FIG. 5 is a general illustration of the operative procedure and FIG. 1 pertains to a specific apparatus, it is seen that the point of input of the beneficial insects is different in these two drawings. In FIG. 1, the injectors are rearward of the J-tube, (relative to airflow input) while in FIG. 5, the input hopper delivers the insects in front of the injectors. While either location for delivery will work for the creation of the compositions of this invention, there is less chance that the hopper input into the mixing chamber will clog with binder, if the input point is to the rear of the flow of binder—the mode of FIG. 1. Note also that the instrumentation such as the various gauges shown in the apparatus have been omitted, since they are only beneficial, not mandatory to carry out the process.

Among the beneficial insects that can be coated in this manner are lacewing eggs, parasitized eggs, wherein the parasite is one of several varieties of the Trichogramma wasp. These include T. Platneri and T. Pretiosum. The host eggs can be either of Sitotroga or Ephestia. Such parasitized eggs are available from insectaries (vendors of bugs) including Rincon-Vitova of Ventura Calif. among others. It is believed that any currently available or future available beneficial insect in the egg, pupa or larva stage can be coated for collection or delivery according to the process of this invention. It is further believed that adult insects such as lady bugs would be impeded in their attempt to eat aphids, if they were coated with the binders of this invention.

Suffice it to say, however, that the binders of this invention do not have the adhesive capability of an epoxy or urethane glue. Thus the force necessary to move collected coated insects from a stratum for placement as by hand or otherwise to a different location can easily be accomplished by hand. Of course, it would be difficult to move just one such coated insect no matter what stage of life the insect is in, due to the tiny size of these beneficial insects.

Among the binders that can be employed in this process are gum arabic, Yes™ glue made by Gane Bros & Lane, Inc. Elk Grove Village, Ill., Elmer's white glue or equal, pectin, gelatin and mucilage, polyvinylpyrollidone (PVPD) and mixtures thereof Solutions generally range from about 7% to about 50% by volume, with 10 to 12.5% being the preferred range. Mucilage, the fluid that comes in little bottles to adhere papers together is available from several sources including Carter in Cambridge Massachusetts and The Borden Company.

Biocarrier, a pectin-based material made by Smuckers Mfg. of Harrisburg Ore. was used favorably with lacewing eggs. Both by aerial (pane and tractor) as well as by backpack sprayer units. However Biocarrier did not work very well with Trichogramma, as the adhesion was poor.

Cloud Cover™ a polymeric solution used to retain moisture in Christmas trees and indoor ornamental plants, and made by Easy Gardner of Waco Tex., was also found to work satisfactorily with lacewings.

The following table illustrates the results of using three different concentrations of the same binder agent for impact upon TG parasitized eggs, which were delivered to a paper target using the apparatus of this invention.

| PVPD | 5% | 10% | 20% |
|---|---|---|---|
| SURVIVAL RATE | 73% | 88% | 82% |
| STICK RATING | 3 | 3 | 3 |
| CLOUDCOVER | 5% | 10% | 20% |
| SURVIVAL RATE | 86% | 84% | 74% |
| STICK RATING | 1 | 2 | 2 |
| MUCILAGE | 5% | 10% | 20% |
| SURVIVAL RATE | 82% | 97% | 90% |
| STICK RATING | 3 | 4 | 4 |
| BIOCARRIER | 5% | 10% | 20% |
| SURVIVAL RATE | 73% | 72% | 70% |
| STICK RATING | 1 | 1 | 1 |

The ratings as noted herein are based upon personal observations of the target papers. The adhesion to a paper target is an indicator of the expected adhesion of the binder coated beneficial insect to the desired substrate, e.g., walnut tree leaves. Survival rate means the percentage of delivered insects that "survived" the trauma of the delivery system to the target. Stick rate is an indication of the relative adhesion of the coated insects to a target surface.

AERIAL DELIVERY

As has been noted previously, the primary intended purpose of the apparatus of this invention is to use it for the aerial delivery of the coated insects to walnut trees primarily and to other trees as well.

Once the apparatus of this invention is mounted to a plane, such as but not limited to the mount plate shown in FIG. 4, the apparatus needs to be actuated. Thus a control panel needs to be in place in the plane which will carry the apparatus.

Reference is now made to FIG. 7 which depicts such a panel. All of the instrumentation and switches to be discussed are conventional in the industry. The discussion centers therefore upon the use of the instruments and switches, of control panel 100 rather than upon their individual novelty.

Switch 101 of the panel 100, is the master on-off switch. This is used just as the name implies, to turn on the apparatus, which has two motors therein, and permits the meter switch and spray switch to each operate.

Switch 102 is the meter switch. It turns on the dispensing system, while switch 103 is the spray switch which permits the fluid to be pumped from the vessel out into the injectors as described elsewhere herein.

Switch 103 controls the injectors to turn the delivery of binder on or off.

Meter 104 is a volt meter which serves as an RPM gauge of the dispensing apparatus motor. The exact speed of the stirrer is of no importance so long as the hopper does not clog up or bridge.

The rheostat 105 is used to regulate the speed of the motor, i.e., the RPM which controls the speed of the dispensing device, i.e., the amount of beneficial insect being delivered to the chamber per unit of time. The rheostat ties in with the meter, in that the meter 104 provides the read out of the variations created by the rheostat's operation.

Pressure gauge 106 is optional and can be used alone or it can be used in conjunction with another such gauge to determine binder spray force.

The optical sensor control 107 has two lights, one to confirm the presence of power since the sensor is electrical and the other to confirm the passage of material from the hopper and is wired to a source of power.

TRACTOR MOUNTING

The apparatus of this invention can also be mounted outboard on a tractor or other field vehicle such as an air blast unit. In such an instance substantially the same control panel 100 would be employed. Since it is easy to stop a tractor to verify hopper delivery visually, the optical sensor can be omitted.

Previously I have related the details of the apparatus and the several changes or variants appliable thereto. The discussion is now directed to the procedure to be employed for the actual delivery of the in-situ prepared binder coated insects by an airplane or tractor mounted apparatus. The reader's attention is drawn to the fact that the apparatus of this invention is generally used in pairs on both tractors and planes, but used singly in conjunction with a hand blower. On a plane, even weight distribution is the reason for tandem usage, while on a tractor, time saving is the prime reason.

SIMULATED ORCHARD APPLICATION

In order to assess the effectiveness of the apparatus of this invention, under actual use conditions, for the delivery of Trichogramma parasitized Ephestia eggs, a collection line was set up using a 15 meter strip of butcher paper, which was marked off into fifteen 1 meter increments (sites), and stapled to sheets of plywood. Butcher paper tents were constructed and stapled to cardstock. The tents were carried to the target zone in plastic bins and were stapled to each site, 180 cm apart and 2.5 cm from either edge of the site, and labeled with test site numbers.

Fresh branches of walnut leaves (5 to 7 leaves each) were placed midway between the tents to simulate the leaves of the orchard canopy. It was necessary to simulate an orchard since this test program was carried out off-season. The target 85, was located perpendicular to the wind as is customary.

The apparatus was attached to the aircraft using a conventional mounting plate. A plastic spray tank fluidly connected to a 12 volt diaphragm pump was placed in the cockpit of the aircraft under the pilot's seat and fluidly connected to a pair of injectors positioned at 45 degrees adjacent to the J-tube disposed in the mixing chamber. This combination was used to transfer a 10% mucilage solution at a pump pressure set at 20 psi, and controlled with a separate on/off switch. The pressure was monitored by a separate pressure gauge located adjacent to the mixing chamber. The nozzles were positioned at two locations to maximize the likelihood of parasitized eggs coming into contact with the adhesive particles. The flow rate of the adhesive delivery system was set at 3.76 gal/min. as the parasitized eggs were set to be metered into the mixing chamber at a rate of about 72.5 mil/min.

The aircraft then took off and made about 7 runs over the target with the eggs being exposed to the mucilage and then delivered by the moving air to the target zone. After each run was made, the sheets were examined with a 7× hand lens for parasitized eggs adhered to the sheet, the locations marked, parasitized eggs counted, and data recorded for each sheet. At the same time, the paper tents and walnut foliage also were collected and taken to the laboratory for incubation for seven days or until all controls had emerged and died. After incubation, locations with parasitized eggs were cut from the sheet with a razor blade and labeled with sheet number. The paper cut-outs then were examined under a Nikon dissecting scope for evidence of the presence of parasitized eggs. A viewing of these eggs determine the existence of little holes where the wasp had emerged. The number of holes serves as an indication of the survival rate of the wasp pupae subsequent to delivery. It is these Trichogramma wasps that are now in the position to attack the eggs of the codling moth.

It was found that the distribution of the mucilage covered parasitized eggs yielded a bell shaped curve. A substantially similar bell curve was obtained when a 50% solution of mucilage was employed. The center of the curves lay closest to the plane with distribution falling off as the distance from the apparatus increased.

An analysis of the data yielded the result when compared to control procedures, without the use of a binder agent to adhere the beneficial insects to the target area, that the survival rate of the pupae of the Trichogramma was substantially the same. That is, the binder created no deleterious effect upon the parasitized eggs, while concentrating their location in the target zone.

The test just discussed is one that as noted simulates walnut orchard conditions. Since the codling moth is in the trees and not on the ground, the structures as described were utilized. The application rate of beneficial insect can be modified as needed to meet the requirements of different conditions, such as different type of tree, or even different variety of the same tree, different wind conditions, different airplane, and even different personal desires of the grower as to the volume of beneficial insect (compositions of this invention) per acre.

It has already been pointed out that the binder can range from about a 10% solution to about a 50% solution when mucilage is utilized. The concentration of beneficial insects can be altered by changing the speed of the metering device, be it the spur gear, or apertured disk or any other dosimeter. The speed of the plane, or the speed of the ground tractor will directly influence the coverage of delivery of the compositions of this invention, given that everything else stays constant. All of these adjustments are within the skill of the artisan.

While I have indicated some of the factors that influence the rate of delivery according to this invention, at this point, the mode of carrying out certain calculations to achieve these changes of delivery will be discussed.

JOB CALCULATIONS

Let us assume that a particular job to be carried out by plane utilizes a plane whose air speed is 120 mph, and that it carries two of the inventive apparatuses. Assume also that the orchard is 100 acres in size, and that the owner desires a density of 100,000 parasitized eggs, or other 100,000 beneficial insects delivered per acre. To obtain the volume of eggs to be delivered, one multiplies the acreage by the density, and divides this by the known volume of a given number of insects. For Trichogramma parasitized eggs of the Ephestia the number is 20K of eggs per ml. Since there are 2 apparatuses to be used simultaneously, that figures. out to 250 ml of eggs per unit.

Given that there are 20,000 eggs/cc with the desired density of 100K eggs per acre that means that 5 ml of eggs must be employed The flying activity of the pilot for his/her passes, switching on the apparatuses over the acreage and turning them off when over neighboring property is beyond the scope of the application. Given that the swath of the pass is 60 feet, then the calculation is made as follows to determine the flow rate of in this case eggs containing the beneficial pest per unit (2 per 120 miles/hr×60 ft./swath×5280 ft/mile×1 acre/43560 sq.ft.×1 hr./60 min.=14.5 acres/min plane) is the 14.5 acres per min ×5 ml=72.5 ml/min; which divided by 2 units on the plane means that 36.25 ml/min/unit is to be delivered by the plane over the target area. The last thing to be calculated, once the known delivery concentration of beneficial insect is known, is the desired flow rate of the binder from the injectors. Since 2 injectors are present per unit, the calculaton pertains to 4 injectors. In my efforts, I used TeeJet nozzles #6503 which operate at about 0.3 gallons per minute under 40 p.s.i. pressure each. Thus 1.2 gallons/min divided by 14.5 acres/min.=0.08 gallons/acre of the binder.

In conclusion it has been found that the aerial delivery of Trichogramma within ephesita eggs, is indeed quite satisfactory, and a sound financial practice. The viability of the beneficial insect is not injured by a through the air delivery, whether aerial by plane or on land by tractor, as well as by use of a hand blower attached to the apparatus. It was further found that the impact of the binder agent upon the beneficial insect had little or no deleterious effect upon the survival rate of the beneficial insect in both the lacewing delivery and the Trichogramma delivery. What was futher found is that the use of the binder did increase the destruction of the pest in the target area as more of the predator were present to do the job than under current practices utilizing hand placed squares of paper with the beneficial insect thereupon within the target area, but on or near the ground, not up in the trees where the pests are and the damage is caused.

While the discusion hereintofore has been primarily dealing with the Trichogramma as a beneficial insect to control codling moth in walnut orchards, it is to be understood that the Trichogramma can be delivered in the same manner to control other detrimental insects with respect to specific crops.

Whereas the TG has been delivered in the format of parasitized eggs of the ephsetia or other insect, I have found that lacewing flies, (Chrysopidae) can be delivered using the process and apparatus of this invention. The larvae of the lacewing are called aphis lions, and are voracious eaters. They feed on aphids, thrips, mites, young corn earworms, and other small soft-bodied insects or eggs. The larvae of the lacewing have sickle-like mandibles which puncture and extract body fluids from their prey.

Delivery of the lacewing is in the egg stage of the insect itself, rather than parasitized in another insect's eggs. Several binders have been utilized in the apparatus of this invention in conjunction with lacewing egg delivery, the best one being mucilage. Lacewings can be used to fight aphids most anywhere. Mention may be made of the acreage of commercial rose growers, vegetable crops, tree crops such as apples, and other crops attacked by detrimental insects; namely, corn by the corn worm.

While separate motors have been shown to turn the stirrer and the metering system (spur gear), it is within the skill of the art to utilize but one motor with appropriate shaft(s) and gear boxes for these two tasks.

While not specifically tested, there is no reason to believe that it would not also be possible to utilize parasitized eggs of the codling moth, to deliver Tgs to an area infested with the grain moth, such as fields of grain bins.

It is to be noted from a review of the drawings of this patent application, that in some instances a reverse venturi was employed at the inlet end of the apparatus. In one variant of the apparatus, the reverse venturi was not employed. The reverse venturi serves merely to slow down the incoming air, such that when the beneficial insects are introduced into the airstream they will not be as adversely impacted if the air is moving at a slower speed, and more time is available for binder and insects to combine. It is beneficial to employ the reverse venturi if the apparatus is to be mounted on a tractor or airplane. Whereas the airspeed of the air from a backpack blower is significantly slower, the use of the reverse venturi for a backpack blower unit, while considered to be within the scope of the invention, is not suggested.

Since certain changes can be made in the above apparatus and process herein discussed without departing from the scope of the invention herein involved, it is intended that all matter contained in the above description and shown in the accompanying drawings shall be interpreted as illustrative and not in a limiting sense.

I claim:

1. An apparatus for the coating and delivery of beneficial insects which comprises:
    a. a hopper for the temporary storage of insects and which hopper has a constricted opening at the bottom in communication with,
    b. an insect metering device for controlling the flow of a determinable finite amount of insects from said hopper,
    c. a delivery tube having an inlet end and an outlet end, and
    d. a tubular chamber having an outlet end and an inlet end for the introduction of air into said chamber, and having at least one fluid injector, disposed within said chamber, for the introduction of a binder solution at a location aft the outlet of the delivery tube, but within said chamber from a source of said solution,
    said metering device in communication with the inlet of the delivery tube; the outlet of the delivery tube being flared and said tube being disposed within the chamber and in communication with the interior of said chamber,
    whereby when air is introduced through the inlet end of the chamber, an airstream is formed that moves through said chamber, and as insects are metered into said delivery tube they are gravity fed to the chamber to be coated by binder solution entering the chamber through said at least one fluid injector, and then the coated insects are expelled through the outlet end of said chamber.

2. The apparatus of claim 1 wherein the metering device comprises a motor operated spur gear.

3. The apparatus of claim 1 wherein the metering device comprises a rotating disk having at least one aperture therein.

4. The apparatus of claim 1 wherein the metering device is in direct communication with a collection bin which in turn is in communication with said delivery tube.

5. The apparatus of claim 4 wherein the collection bin has a spout that communicates with the inlet of the collection tube.

6. The apparatus of claim 1 wherein the delivery tube comprises a J-shaped tube the outlet of which is disposed elevationally at about the middle of the chamber and which is directed toward the outlet of the chamber.

7. The apparatus of claim 1 wherein the delivery tube is a J-shaped tube having a flared outlet end, said outlet of which is directed toward the outlet of the chamber and the metering device comprises a rotor.

8. The apparatus of claim 1 wherein each binder solution injector is disposed at a about a 45 degree angle toward the outlet of said chamber.

9. The apparatus of claim 1 further including a stirrer mounted for rotation within the hopper to prevent the clogging thereof.

10. An apparatus for the coating and delivery of beneficial insects which comprises:
    a. a hopper for the temporary storage of the beneficial insects and which hopper has a constricted opening at the bottom in communication with,
    b. an insect metering device for controlling the flow of a determinable amount of insects from said hopper,
    c. a collection bin to receive said insects, in communication with said metering device,
    d. a delivery tube having an inlet end and a flared outlet end, and
    e. a tubular chamber having an outlet end and an inlet end for the introduction of air into said chamber, and having at least one fluid injector, disposed within said chamber, for the introduction of a binder solution; into an airstream, aft the outlet of said delivery tube but within said chamber,
    said collection bin in communication with the inlet of the delivery tube; the outlet of the delivery tube being disposed within the chamber and in communication with the interior of said chamber,
    whereby when air is introduced through the inlet end of the chamber, an airstream is formed that moves through said chamber, and as insects are metered into said delivery tube they are gravity fed to the chamber to be coated by binder solution entering the chamber through said at least one fluid injector, and then the coated insects are expelled through the outlet end of said chamber.

11. The apparatus of claim 10 wherein the metering device comprises a motor operated spur gear.

12. The apparatus of claim 10 wherein the metering device comprises a rotating disk having at least one aperture therein.

13. The apparatus of claim 10 further including a stirrer mounted for rotation within the hopper to prevent the clogging thereof.

14. The apparatus of claim 10 wherein the collection bin has a spout that communicates with the inlet of the delivery tube and further wherein the delivery tube is a J-shaped tube the outlet of which is directed toward the outlet of said chamber.

15. The apparatus of claim 10 further including an optical sensor, connected to a power source, mounted at the inlet end of the delivery tube to monitor the flow into the delivery tube.

16. The apparatus of claim 15 wherein there are two injectors mounted in opposed position, each of which is directed at a 45 degree angle toward the outlet of the chamber.

17. The apparatus of claim 10 wherein the hopper, metering device and collection bin are all disposed within a housing, having an opening therein in communication with said hopper.

18. The apparatus of claim 10 further including means for mounting the apparatus to an airplane.

19. The apparatus of claim 10 wherein the chamber's inlet end is configured as a reverse venturi and the delivery tube has an outwardly flared outlet.

20. The apparatus of claim 10 further including a pressure regulator in fluid communication with the at least one injector to control the flow of binder to the at least one injector.

21. The apparatus of claim 10 further including blower means connected to the inlet end of the chamber.

22. An apparatus for the aerial delivery of binder coated beneficial insects which comprises:
   a. a hopper for the temporary storage of the insects and which hopper has a constricted opening at the bottom in communication with,
   b. an insect metering device for periodically dispensing a finite amount of insects from said hopper,
   c. a collection bin to receive said insects, in communication with said metering device,
   d. a J-shaped delivery tube having an inlet end and a flared outlet end,
   e. an optical sensor encircling said delivery tube, connected to a power source, and adapted to monitor the flow though said delivery tube,
   f. a tubular chamber having an outlet end and a reverse venturi configured inlet end for the introduction of air into said chamber, and having at least a pair of fluid injectors, oppositely disposed within said chamber, for the introduction of a binder solution, into an airstream aft the outlet of said delivery tube but within said chamber,
   said collection bin in communication with the inlet of the delivery tube; the outlet of the delivery tube being disposed within the chamber and in communication with the interior of said chamber,
   whereby when air is introduced through the inlet end of the chamber, an airstream is formed that moves through said chamber, and as insects are metered into said delivery tube they are fed to the chamber to be coated by binder solution entering the chamber through at least one of said pair of fluid injectors, and then the coated insects are expelled through the outlet end of said chamber.

23. The apparatus of claim 22 further including a motorized stirrer disposed in said hopper to prevent clogging of the constricted opening, and the metering device comprises a motorized spur gear.

24. The apparatus of claim 22 further including coupling means for mounting a backpack blower thereto.

25. The apparatus of claim 22 including means for mounting the apparatus on one of an airplane and a tractor.

26. The process of controlling insect pests on an infested specific crop which comprises:
   a. introducing a plurality of beneficial insects into a moving airstream within a chamber having an air inlet and an air outlet, parallel to the movement of the airstream,
   b. injecting a binder solution into the airstream,
   c. coating the moving beneficial insects with the binder solution, aft the entry thereof, but within said chamber,
   d. expelling the coated insects from the airstream through the outlet of the chamber onto the specific crop.

27. The process of delivering beneficial insects to the foliage of infested target trees which comprises:
   a. mounting at least one tubular chamber, each of which has an air inlet end and an air outlet end onto an airplane, with the air inlet of each chamber facing forward,
   b. placing a finite amount of the beneficial insects into a hopper in communication with the chamber,
   c. metering a determinable continuous supply of beneficial insects into the chamber from the hopper in a direction parallel to a flow of air through the chamber while flying over the target trees,
   d. injecting a binder solution into the chamber during the time the beneficial insects are in the chamber,
   e. coating the beneficial insects with the binder solution, within the chamber, aft the entry of the insects,
   f. expelling the coated insects out the outlet of the chamber onto the target trees.

28. The process of claim 27 including the extra step of monitoring the flow of the insects into the chamber by optically sensing the flow.

29. The process of claim 27 including the step of slowing down the speed of the air entering each chamber prior to the introduction of the beneficial insects thereto.

30. The process of claim 29 wherein the injecting of the binder solution transpires at a 45 degree angle to the flow of the insects within the chamber.

* * * * *